US012721525B2

(12) United States Patent
Palero et al.

(10) Patent No.: US 12,721,525 B2
(45) Date of Patent: Sep. 1, 2026

(54) SYSTEMS AND METHODS FOR ILLUMINATING TISSUE

(71) Applicant: KONINKLIJKE PHILIPS N.V., Eindhoven (NL)

(72) Inventors: Jonathan Alambra Palero, Waalre (NL); Mathivanan Damodaran, 'S-Hertogenbosch (NL); Yannyk Parulian Julian Bourquin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 143 days.

(21) Appl. No.: 18/567,450

(22) PCT Filed: May 30, 2022

(86) PCT No.: PCT/EP2022/064519

§ 371 (c)(1),
(2) Date: Dec. 6, 2023

(87) PCT Pub. No.: WO2022/258407

PCT Pub. Date: Dec. 15, 2022

(65) Prior Publication Data

US 2024/0268677 A1 Aug. 15, 2024

(30) Foreign Application Priority Data

Jun. 9, 2021 (EP) .................................... 21178576

(51) Int. Cl.
*A61B 5/00* (2006.01)

(52) U.S. Cl.
CPC ............ *A61B 5/0077* (2013.01); *A61B 5/445* (2013.01); *A61B 5/725* (2013.01)

(58) Field of Classification Search
CPC ........ A61B 5/0077; A61B 5/445; A61B 5/725
See application file for complete search history.

(56) References Cited

U.S. PATENT DOCUMENTS

| | | | |
|---|---|---|---|
| 5,590,660 | A | 1/1997 | Macaulay et al. |
| 9,648,254 | B2 | 5/2017 | Darty et al. |

(Continued)

FOREIGN PATENT DOCUMENTS

| | | | |
|---|---|---|---|
| JP | 2010176992 | A | 8/2010 |
| WO | 2015128205 | A1 | 9/2015 |
| WO | 2019148268 | A1 | 8/2019 |

OTHER PUBLICATIONS

Safrani et al., "Skin biomedical optical imaging system using dual-wavelength polarimetric control with liquid crystals", Journal of Biomedical Optics 15, 2, 026024, Mar./Apr. 2010, pp. 026024-1-026024-8.

(Continued)

*Primary Examiner* — Sean A Frith

(57) ABSTRACT

The invention discloses a tissue illumination system (700). The tissue illumination system (700) includes at least one radiation source (702) configured to generate first radiation in a first wavelength band at a first intensity, the first radiation having a peak wavelength, λ1; and second radiation in a second wavelength band at a second intensity, the second radiation having a peak wavelength, λ2. An intensity ratio of the first intensity relative to the second intensity is between 0.2 and 1; and the peak wavelength λ1 of the first wavelength band and the peak wavelength λ2 of the second wavelength band are selected such that they satisfy the following relationships: Formula (I). The tissue illumination system (700) also includes a radiation delivery unit (404) configured to deliver the first radiation and the second radiation towards tissue of a subject. An optical filter system, a device, a tissue illumination method and a computer program product are also disclosed.

(Continued)

$$\begin{cases} 640 \leq \lambda_1 \leq 740 \text{ (nm)} \\ 470 \leq \lambda_2 \leq 530 \text{ (nm)} \\ \lambda_1 \geq \frac{3816}{\lambda_3 - 425} + 594 \text{ (nm)} \\ \lambda_1 \leq \frac{7694}{\lambda_2 - 425} + 594 \text{ (nm).} \end{cases} \quad \text{(I)}$$

15 Claims, 10 Drawing Sheets

(56) References Cited

U.S. PATENT DOCUMENTS

2015/0271380 A1* 9/2015 Darty ...................... G01J 3/108
348/342
2015/0374277 A1 12/2015 Patwardhan
2017/0156673 A1* 6/2017 Uchida ................ G06V 10/141
2019/0099613 A1* 4/2019 Estes .................... A61N 5/0616

OTHER PUBLICATIONS

Alex et al, "3D optical coherence tomography for clinical diagnosis of nonmelanoma skin cancers", Imaging Med. (2011) 3(6), 653-674.
International Search report and Written Opinion of PCT/EP2022/064519, dated Aug. 19, 2022.

* cited by examiner 200
(a)
210
(b)
210
(c)
230
(d)
Emission band A peak wavelength (nm)
Emission band B peak wavelength (nm)

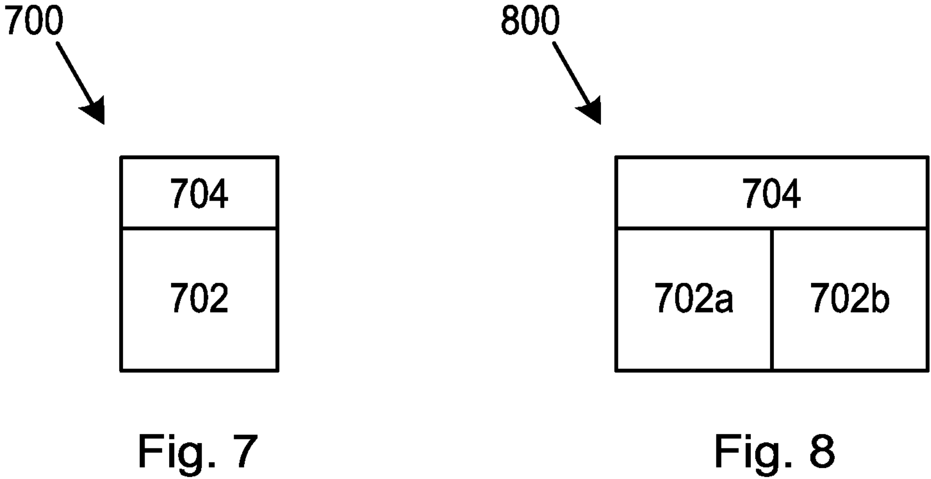
Fig. 7
Fig. 8
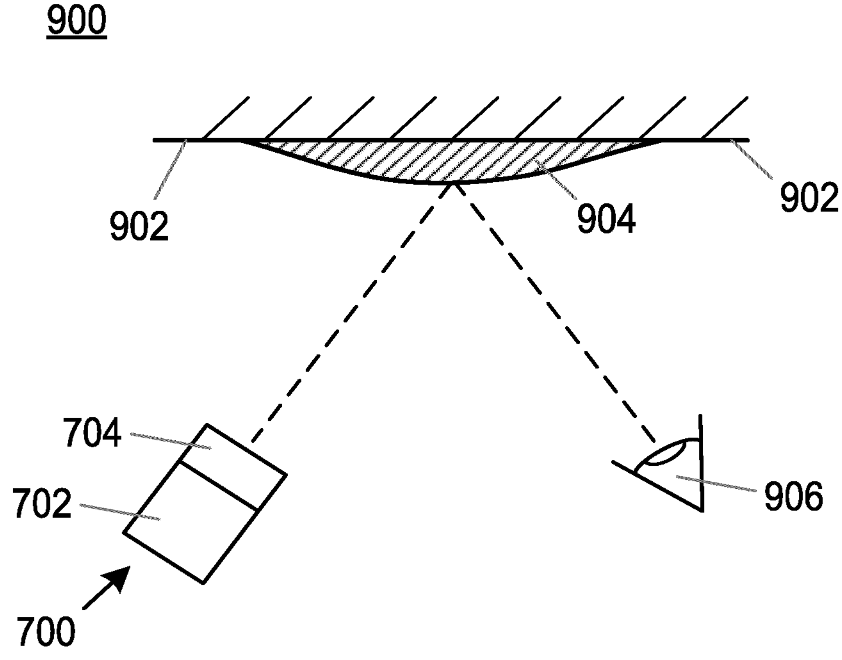
Fig. 9

SYSTEMS AND METHODS FOR ILLUMINATING TISSUE

CROSS-REFERENCE TO PRIOR APPLICATIONS

This application is the U.S. National Phase application under 35 U.S.C. § 371 of International Application No. PCT/EP2022/064519, filed on May 30, 2022, which claims the benefit of European Patent Application No. 21178576.1, filed on Jun. 9, 2021. These applications are hereby incorporated by reference herein.

FIELD OF THE INVENTION

The invention relates to systems and methods for illuminating tissue and, more particularly, to systems and methods for illuminating tissue with radiation in two distinct wavelength bands or filtering radiation in two distinct wavebands.

BACKGROUND OF THE INVENTION

Many personal care activities and skin measurement and monitoring activities involve a person viewing or inspecting their own skin or the skin of another person. For example, a person may view their reflection in a mirror, or a representation of their face or body on the screen of a computing device (e.g. a tablet computer) or an imaging device (e.g. a camera while performing a personal care activity, such as applying make-up. Similarly, a medical professional may inspect the skin of another person when assessing the person for an injury or illness, such as bruising or inflammation of part of the body.

Under broadband light (e.g. white light), it can be difficult for the human eye to distinguish clearly between inflamed tissue and uninflamed tissue. The reason for the inability of the naked human eye to clearly identify the boundary between inflamed and uninflamed regions of tissue is due to the fact that the spectral signatures of these different regions of tissue are averaged and smoothed out by broadband light. This, in combination with the wide-spectral properties of the L-, M- and S-cones of the human retina, results in poor contrast between inflamed and uninflamed regions of tissue when broadband light is used.

There is, therefore, a need for a system which enables the human eye to more clearly distinguish between inflamed and uninflamed regions of tissue.

SUMMARY OF THE INVENTION

It would be advantageous to be able to better distinguish between regions of tissue that are inflamed and regions of tissue that are not inflamed. This would allow better visibility of bruises, spots, and other lesions and inflammations of skin or tissue. It has been recognized by the inventors that such regions can be more readily distinguished from one another using a combination of light having particular characteristics. For example, it has been recognized that blood-rich regions of tissue (e.g. lips, inflamed spots or pimples, and regions of skin irritation) appear redder when illuminated with a combination of green and red light. Using a combination of radiation in particular wavebands, or broadband radiation filtered leave a combination of radiation in the particular wavebands, can further improve the distinction between the inflamed and uninflamed regions.

According to a first aspect, the present invention provides a tissue illumination system comprising at least one radiation source configured to generate: first radiation in a first wavelength band at a first intensity, the first radiation having a peak wavelength, $\lambda_1$; and second radiation in a second wavelength band at a second intensity, the second radiation having a peak wavelength, $\lambda_2$; and a radiation delivery unit configured to deliver the first radiation and the second radiation towards tissue of a subject; wherein an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

If the generated radiation (e.g. the first radiation and the second radiation) is used to illuminate inflamed and uninflamed regions of tissue of the subject, then the contrast between these tissue regions becomes more enhanced, such that a viewer of the subject is able to more clearly see the distinction between the different regions. Under white light/broadband radiation, inflamed tissue regions may be harder to distinguish from uninflamed tissue regions to a human viewer.

In some embodiments, the first radiation and the second radiation may each have a spectral full-width-at-half-maximum of between 40 nm and 150 nm.

The tissue illumination system may, in some embodiments, further comprise a polarizer to linearly polarize the radiation after it is emitted from the at least one radiation source or after the radiation has been reflected from the tissue of the subject. In some embodiments, the tissue illumination system may comprise a first polarizer to linearly polarize the radiation after it is emitted from the at least one radiation source and a second polarizer to linearly polarize, in a direction perpendicular relative to the polarization direction of the first polarizer, radiation reflected from the tissue of the subject.

In some embodiments, the tissue illumination system may further comprise one or more sensors configured to measure a light intensity and/or a color temperature of ambient light at or in the vicinity of the tissue of the subject. The tissue illumination system may further comprise a processor operatively coupled to the at least one radiation source. The processor may be configured to adjust, based on an output of the one or more sensors, one or more of: an intensity of radiation generated by the at least one radiation source; and an intensity ratio of the first intensity relative to the second intensity.

The tissue illumination system may further comprise an image capture device configured to receive radiation reflected from the tissue of the subject.

According to a second aspect, the present invention provides an optical filter system comprising at least one bandpass filter configured to enable transmission of: first radiation in a first wavelength band at a first intensity, the first radiation having a peak wavelength, $\lambda_1$; and second radiation in a second wavelength band at a second intensity, the second radiation having a peak wavelength, $\lambda_2$; wherein the at least one bandpass filter is configured to enable transmission of the first radiation and the second radiation such that an intensity ratio of the first intensity relative to the second intensity is between 0.2 and 1; and wherein the peak wavelength $\lambda_1$, of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \frac{3816}{\lambda_2 - 425} + 594 \text{ (nm)} \\ \lambda_1 \le \frac{7694}{\lambda_2 - 425} + 594 \text{ (nm)} \end{cases}.$$

In some embodiments, the at least one bandpass filter may be configured to enable transmission of the first radiation and the second radiation such that the first radiation and the second radiation each have a spectral full-width-at-half-maximum of between 40 nm and 150 nm.

According to a third aspect, the present invention provides a device comprising a tissue illumination system having at least one broadband radiation source. The at least one radiation source of this device being configured to generate broadband radiation including a first radiation having a wavelength, $\lambda_1$; and a second radiation having a peak wavelength, $\lambda_2$. The device further comprising a radiation delivery unit configured to deliver the broadband radiation to the tissue of the subject, and an optical filter system as discussed above.

The optical filter system might be positioned to filter the broadband radiation after the broadband radiation is emitted from the at least one radiation source and before it is reflected from the tissue of the subject, or to filter the broadband radiation after the radiation has been reflected from the tissue of the subject.

The device may comprise a medical instrument, a mirror, a headset or a mask.

According to a fourth aspect, the present invention provides a tissue illumination method comprising generating first radiation in a first wavelength band at a first intensity, the first radiation having a peak wavelength, $\lambda_1$; generating second radiation in a second wavelength band at a second intensity, the second radiation having a peak wavelength, $\lambda_2$; and delivering the radiation in the first radiation and the second radiation towards tissue of a subject; wherein an intensity ratio of the second intensity relative to the first intensity is between 0.2 and 1; and wherein the peak wavelength $\lambda_1$, of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \frac{3816}{\lambda_2 - 425} + 594 \text{ (nm)} \\ \lambda_1 \le \frac{7694}{\lambda_2 - 425} + 594 \text{ (nm)} \end{cases}.$$

In some embodiments, the tissue illumination method may further comprise measuring one or more of a light intensity and a color temperature of ambient light at or in the vicinity of the tissue of the subject; and adjusting, based on the measured light intensity and/or on the measured color temperature, one or more of an intensity of the first radiation and/or the second radiation, and an intensity ratio of the first intensity relative to the second intensity.

According to a fifth aspect, the present invention provides a computer program product comprising a non-transitory computer-readable medium, the computer-readable medium having computer-readable code embodied therein, the computer-readable code being configured such that, on execution by a suitable computer or processor, the computer or processor is caused to: operate at least one light source to generate first radiation in a first wavelength band at a first intensity to be delivered to tissue of a subject, the first radiation having a peak wavelength, $\lambda_1$; and operate the at least one light source to generate second radiation in a second wavelength band at a second intensity to be delivered to the tissue of a subject, the second radiation having a peak wavelength, $\lambda_2$; wherein an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \frac{3816}{\lambda_2 - 425} + 594 \text{ (nm)} \\ \lambda_1 \le \frac{7694}{\lambda_2 - 425} + 594 \text{ (nm)} \end{cases}.$$

The first radiation and the second radiation may each have a spectral full-width-at-half-maximum of between 40 nm and 150 nm.

The computer-readable code may be further configured such that, on execution by a suitable computer or processor, the computer or processor is caused to: receive sensor data indicative of a light intensity and/or a color temperature of ambient light at or in the vicinity of the tissue of the subject; and adjust, based on the received sensor data, one or more of: an intensity of radiation generated by the at least one radiation source; and an intensity ratio of the first intensity relative to the second intensity.

These and other aspects of the invention will be apparent from and elucidated with reference to the embodiments described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 7 is a schematic illustration of an example of a tissue illumination system;

FIG. 8 is a schematic illustration of a further example of a tissue illumination system;

FIG. 9 is a schematic illustration of an example of a tissue illumination system illuminating a region of inflamed tissue;

DETAILED DESCRIPTION OF THE EMBODIMENTS

Embodiments disclosed herein provide a mechanism by which inflamed tissue may be distinguished more readily from uninflamed or less inflamed tissue by a human viewer. Under white or broadband light, such a distinction may be more difficult, due to the way such light is reflected from the tissue and received by photoreceptors in the eye of a human. However, by applying the systems and methods disclosed herein, it is possible to clearly distinguish between these types of tissue. As used herein, the term "tissue" is intended to refer to any part of the human or animal body tissue, such as skin.

Figure 2:
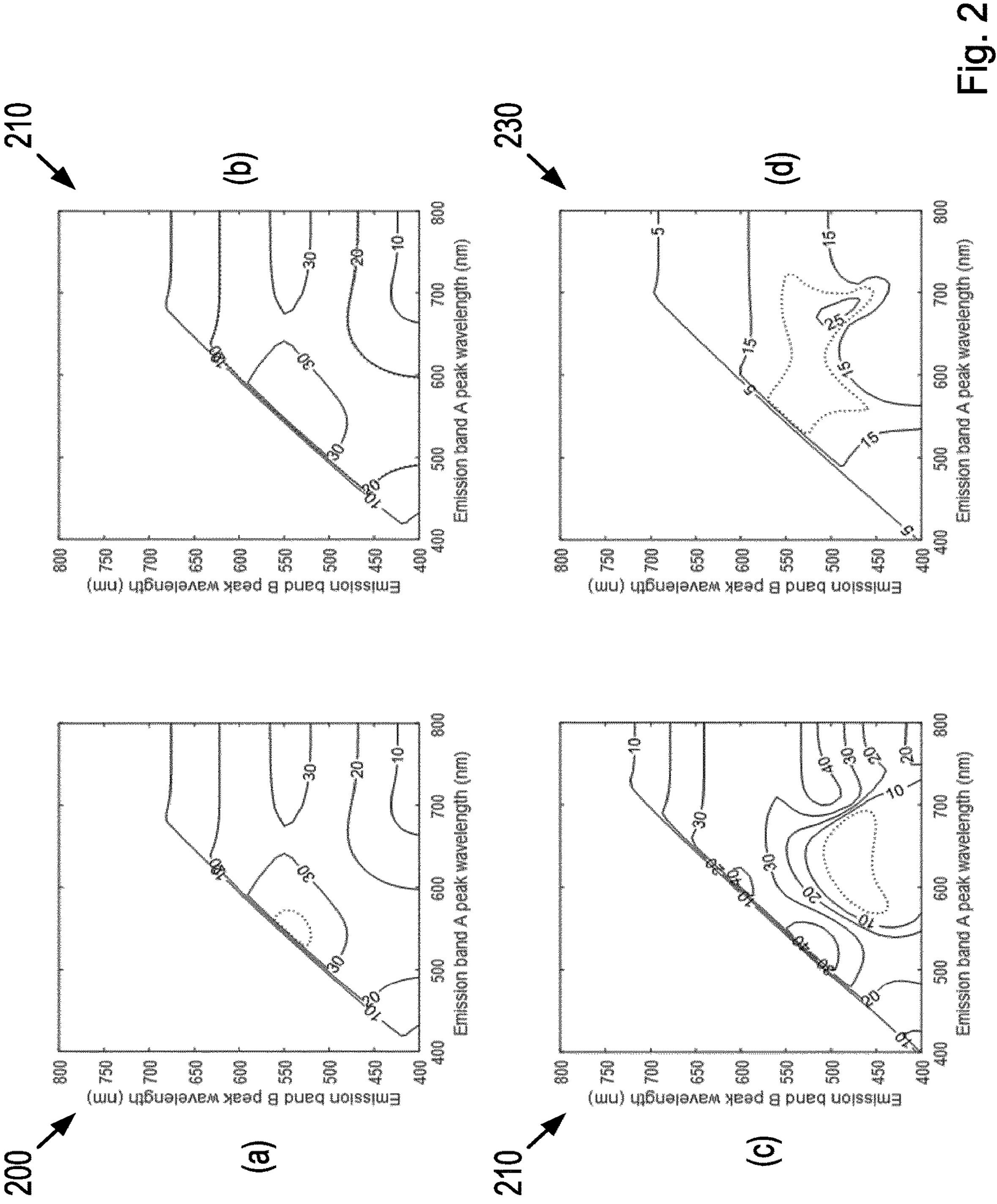
FIG. 2 is a series of plots showing perceived color difference and perceived contrast for radiation of two different wavelengths.
Figure 3:
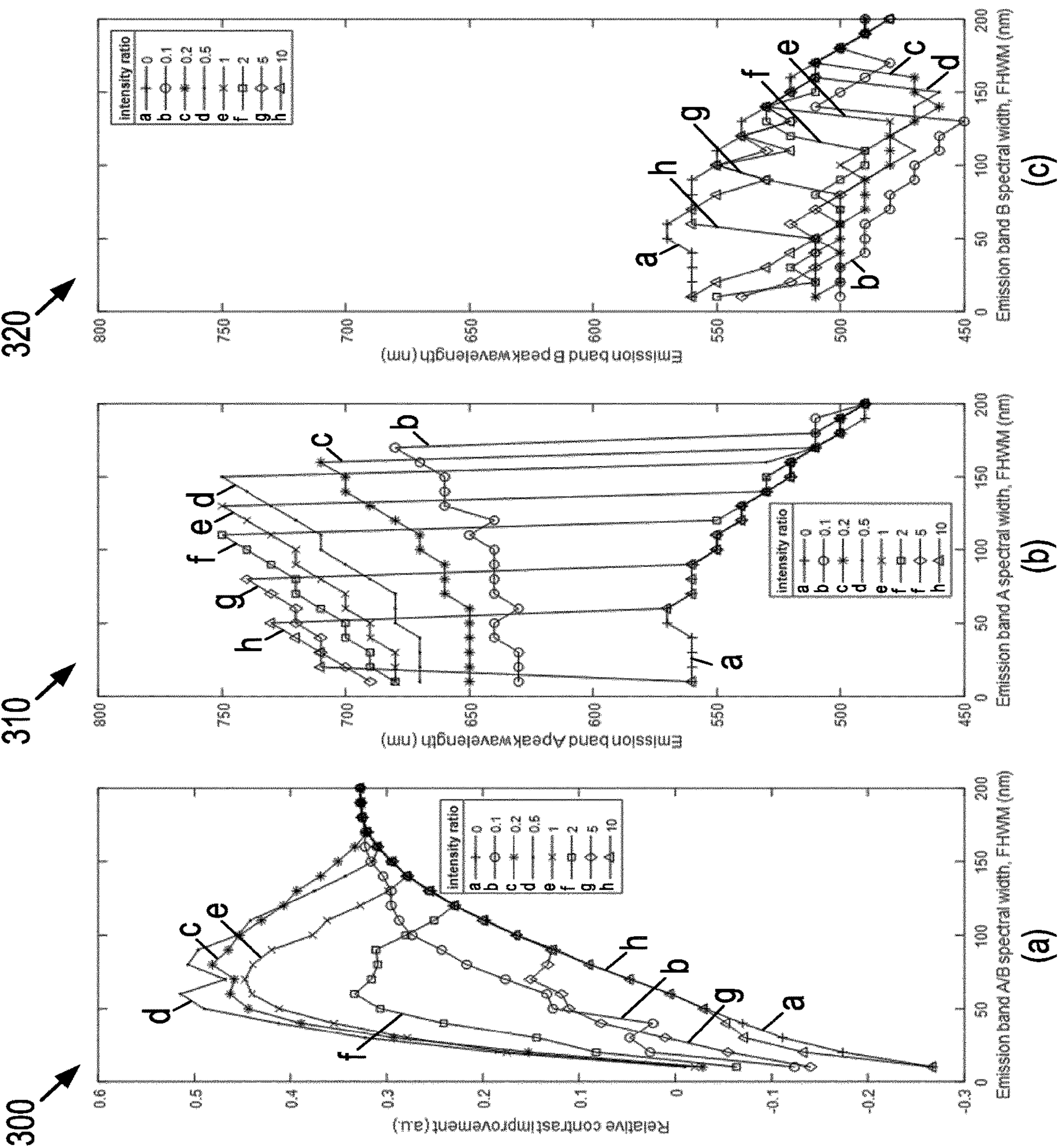
FIG. 3 is a series of plots showing various characteristics of radiation at different intensity ratios.

The inventors of the present disclosure have recognized that combinations of radiation in certain wavebands can be particularly helpful to a person hoping to be able to distinguish between regions of inflamed tissue (e.g. blood-rich tissue) and regions of uninflamed tissue. Through a number of simulations, the inventors were able to determine the particular wavebands of radiation which, when combined, improve the contrast between the inflamed and uninflamed regions of tissue. Graphs showing the outputs of the various simulations are shown in FIGS. 1 to 3.

Figure 1:
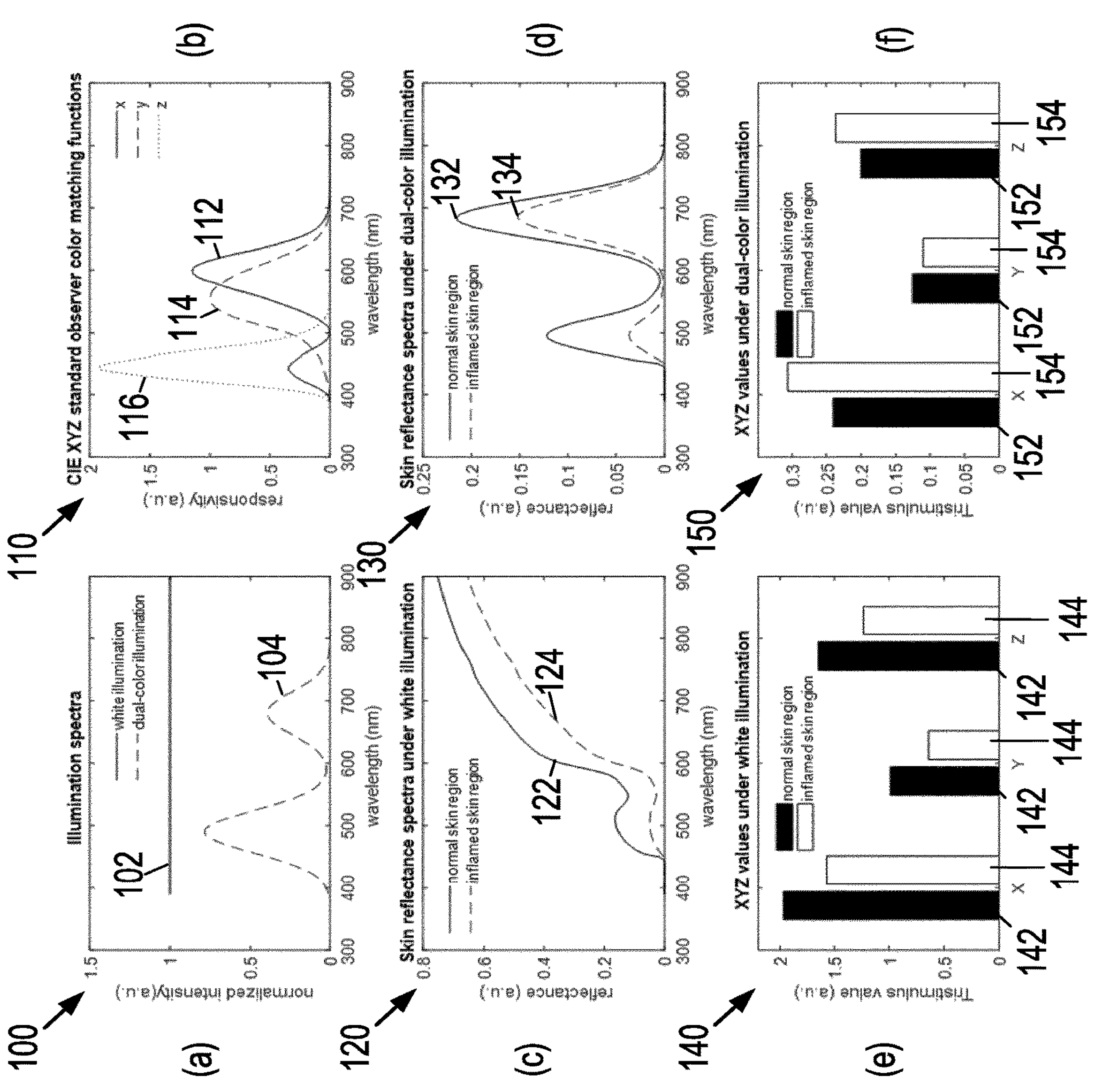
FIG. 1 is a series of plots showing visual contrast of inflamed and un-inflamed tissue regions when illuminated using white light and dual-color illumination.

FIG. 1 is a series of graphs showing the visual contrast of inflamed and uninflamed tissue regions when illuminated using white light (e.g. broadband light) and dual-color radiation. FIG. 1*a* is a graph 100 showing the relative intensities of the white light 102 and the dual color radiation 104 used during the simulations. While the white light 102 has a constant relative intensity for all visible wavelengths, the intensity of the dual-color radiation peaks at the wavelengths of red light and green light. Specifically, the dual-color radiation included radiation having a first peak wavelength of 680 nanometers (n), with a full-width-at-half maximum (FWHM) of 80 nm, and a second peak wavelength of 490 nm, with an FWHM of 80 nm. The dual-color radiation used in the simulation had an intensity ratio of 0.5:1 (i.e. the radiation having the peak wavelength at 490 nm was provided at double the intensity of the radiation having the peak wavelength at 680 nm). The two types of radiation were used in the simulation to illuminate two regions of tissue: a region of regular, uninflamed tissue, and a region of inflamed tissue.

FIG. 1*b* is a graph 110 showing observations of two different tissue regions, described numerically using color-matching functions as defined in the International Commission on Illumination (CIE). The CIE color-matching functions, $\overline{x}(\lambda)$, $\overline{y}(\lambda)$ and $\overline{z}(\lambda)$, represent a numerical description of the chromatic response of the observer. The functions may be considered to be the spectral sensitivity curves of the three linear light detectors, yielding the CIE tristimulus values X, Y and Z. In FIG. 1*b*, value X is represented by the line 112, value Y is represented by the line 114 and value Z is represented by the line 116. The CIE color-matching functions are, collectively, referred to as the CIE standard observer.

FIGS. 1*c* and 1*d* show, respectively, graphs 120 and 130 of reflectance spectra for white light (FIG. 1*c*) and dual-color radiation (FIG. 1*d*) for inflamed and uninflamed tissue regions. In the graph 120, line 122 represents the reflectance from the uninflamed tissue region, and line 124 represents the reflectance from the inflamed tissue region. In the graph 130, line 132 represents the reflectance from the uninflamed tissue region, and line 134 represents the reflectance from the inflamed tissue region. FIGS. 1*e* and 1*f* show, respectively, graphs 140 and 150 of corresponding tristimulus values for white light (FIG. 1*e*) dual-color radiation (FIG. 1*f*). In the graph 140, the data bars 142 represent the tristimulus value in respect of the uninflamed tissue region, and the data bars 144 represent tristimulus value in respect of the inflamed tissue region. In the graph 150, the data bars 152 represent the tristimulus value in respect of the uninflamed tissue region, and the data bars 154 represent tristimulus value in respect of the inflamed tissue region. From the tristimulus values shown in the graphs 140 and 150, it can be observed that the difference in relative ratios of X, Y and Z values between reflections from inflamed and uninflamed tissue regions are larger when dual-color radiation is used than when white light is used. This difference in relative ratios can be quantified by calculating the resulting color difference or distance metric between the inflamed and uninflamed tissue regions.

FIG. 2 is a series of contour plots showing perceived color difference and perceived contrast between inflamed and uninflamed tissue regions, for different peak-wavelength combinations of two light sources with equal intensities and equal spectral widths (FWHM) of 80 nm. FIG. 2*a* shows a contour plot 200 of the calculated perceived contrast in terms of lightness, L, FIG. 2*b* shows a contour plot 210 of the calculated perceived contrast in terms of hue, H, FIG. 2*c* shows a contour plot 220 of the calculated perceived contrast in terms of chroma, C, and a FIG. 2*d* shows a contour plot 230 of the calculated perceived total contrast (denoted delta E, or dE94, in accordance with the standard CIE 1994). In FIG. 2, "Emission band A" corresponds to wavelengths in a first emission band (wavelengths in the red part of the visible spectrum), and "Emission band B" corresponds to wavelengths in a second emission band (wavelengths in the green part of the visible spectrum). The dotted line shown in the plots of FIG. 2 represent iso-lines corresponding to the contrast between inflamed and uninflamed tissue regions when illuminated by white radiation. It is evident from the plot 230 in FIG. 2*d* that the total perceived contrast between the inflamed and uninflamed tissue regions is larger, relative to white radiation, when dual-color radiation is used which has peak wavelengths at 490 nm and 680 nm.

FIG. 3 is a series of plots showing how the relative contrast varies as a function of the spectral width (i.e. FWHM). FIG. 3*a* shows a plot 300 of the relative contrast improvement as a function of FWHM for various intensity ratios. FIG. 3*b* shows a plot 310 of wavelengths in the first emission band (i.e. "Emission band A"—wavelengths in the red part of the visible spectrum) as a function of FWHM for various intensity ratios, and FIG. 3*c* shows a plot 320 of wavelengths in the a second emission band (i.e. "Emission band B"—wavelengths in the green part of the visible spectrum) as a function of FWHM for various intensity ratios. From the plot 300 in FIG. 3*a*, it is evident that the relative contrast improvement peaks when the spectral band-width is at approximately 80 nm. The plot 300 also indicates that the optimum intensity ratio is 0.5, and that strong contrast improvements can also be seen when intensity ratios of 0.2 and 1 are used. The relative contrast improvement reduces when the intensity ratio is reduced 0.1 or lower, or increased to 2 or more. Thus, the optimum contrast improvement is seen with intensity ratios of between 0.2 and 1.

Based on the outputs of the various simulations, it is possible to determine ranges of peak wavelengths, ranges of spectral widths, and optimal intensity ratios that give rise to an improvement in the contrast between inflamed and uninflamed tissue regions. Table 1 below summarizes optimal parameter ranges for two emission bands that give rise to an improvement in the contrast of greater than 30%.

TABLE 1

| Intensity ratio | Spectral width range | First peak wavelength range | Second peak wavelength range | Maximum contrast improvement (%) |
|---|---|---|---|---|
| 0.2 | 70 nm-150 nm | 640 nm-680 nm | 470 nm-490 nm | 48% |
| 0.5 | 40 nm-140 nm | 670 nm-740 nm | 470 nm-510 nm | 51% |
| 1.0 | 50 nm-100 nm | 680 nm-720 nm | 490 nm-530 nm | 45% |

Figure 4:
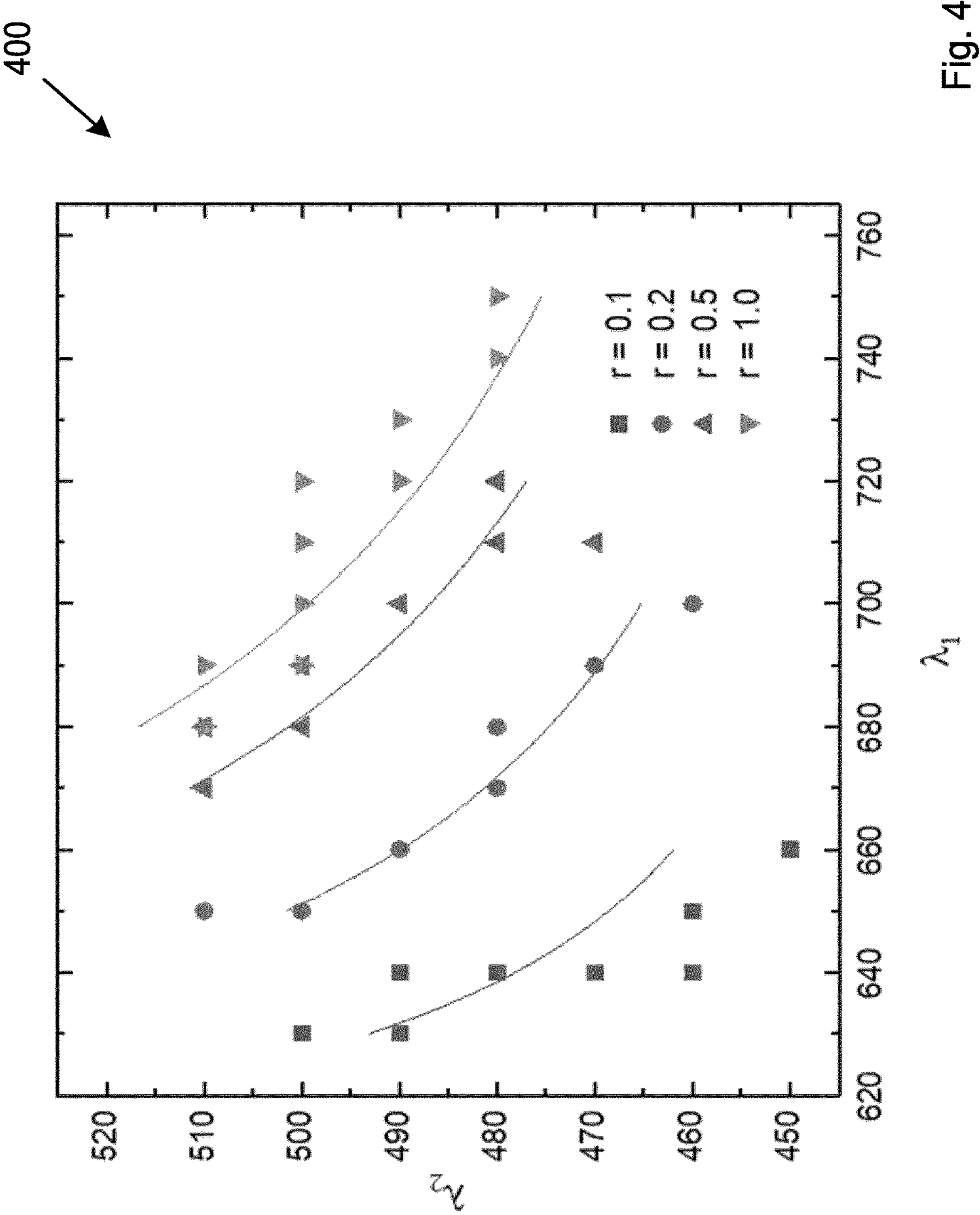
FIG. 4 is a chart showing data from FIG. 3 replotted for different ratio values.

FIG. 4 is a chart 400 showing data from FIGS. 3*b* and 3*c* replotted for different ratio values, r. The data are the fitted with a rational function, $$y = a + \frac{A}{(x+b)},$$

where fitted values are: α=425±5 nm and b=−594±5 nm, and the values for A are ratio-dependent. Table 2 below shows how A varies for different ratios, r.

TABLE 2

| Intensity ratio, r | A |
|---|---|
| 0.1 | 2214 |
| 0.2 | 3816 |
| 0.5 | 6421 |
| 1 | 7694 |

Substitution of the variable y for $\lambda_2$ and of the variable x for $\lambda_1$ gives:

$$A = (\lambda_1 - 594 \text{ nm})(\lambda_2 - 425 \text{ nm}) \quad \text{(Equation 1)}$$

Figure 5:
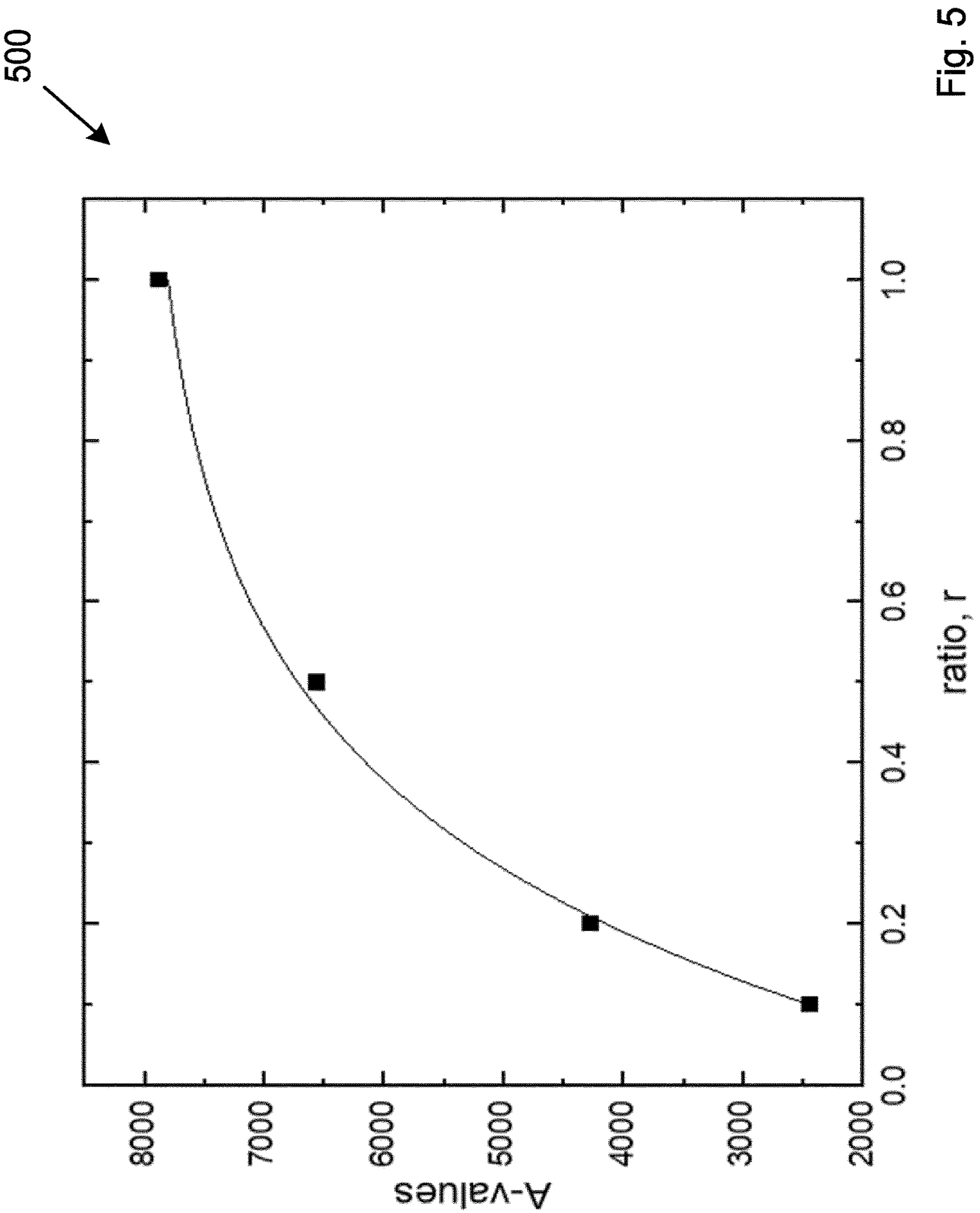
FIG. 5 is a plot of A-values as a function of the intensity ratio, r.

FIG. 5 is a chart 500 showing the values of A from Table 2 above plotted as a function of their respective ratio values, r. The curve fitted to the data in the chart 500 fits the function:

$$A = c\left(1 - e^{-r/t}\right) \quad \text{(Equation 2)}$$

where fitted values are: c=8009±176 and t=0.2738±0.0161. Combining Equations 1 and 2, gives:

$$c\left(1 - e^{-r/t}\right) = (\lambda_1 - 594)(\lambda_2 - 425) \quad \text{(Equation 3)}$$

-continued $$\left(e^{-\frac{r}{t}}\right) = 1 - B(\lambda_1 - 594)(\lambda_2 - 425), \quad \text{(Equation 4)}$$

where B=1/c=0.000125, and $$r = -t \cdot \ln(1 - B(\lambda_1 - 594)(\lambda_2 - 425)) \quad \text{(Equation 5)}$$

Equation 5 relates a peak wavelength $\lambda_1$ within a first wavelength band (e.g. 640 nm to 720 nm), a peak wavelength $\lambda_2$ within the second wavelength band (e.g. 470 nm to 530 nm) and r the relative intensity ratio between $\lambda_1$ and $\lambda_2$. Thus, Equation 5 can be used to determine an intensity ratio r, given peak wavelengths $\lambda_1$ and $\lambda_2$ in the first and second wavelength bands respectively. If the relative intensity ratio r is within the range 0.2 to 1, then the combination of $\lambda_1$, $\lambda_2$ and r is considered to provide good contrast between inflamed and uninflamed tissue regions.

Figure 6:
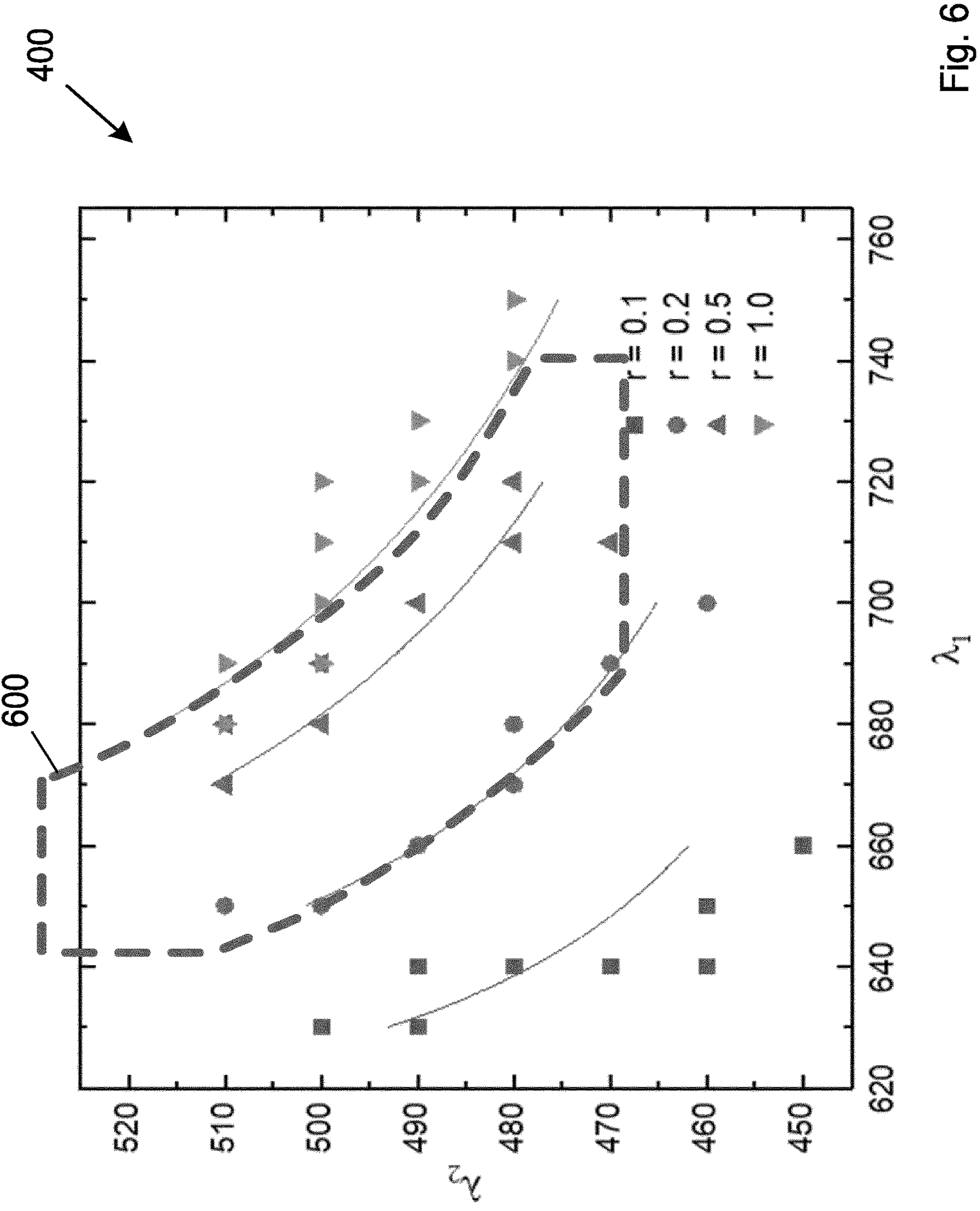
FIG. 6 is a chart showing the chart of FIG. 4 with a region indicating points falling with a given parameter range.

FIG. 6 shows the chart 400 of FIG. 4, with an additional region 600 indicated by a dashed line. Data points falling within the region 600 have parameters of $\lambda_1$ falling within the intended waveband of 640 nm to 740 nm, $\lambda_2$ falling within the intended waveband of 470 nm to 530 nm and r falling within the intended range of intensity ratios 0.2 to 1. Thus, points falling within the region 600 correspond to radiation that would illuminate tissue regions in such a way that the human eye would see a good contrast between inflamed and uninflamed regions of tissue.

The intended ranges of the first wavelength band and the second wavelength band can be expressed independently of the intensity ratio. From Table 2 above, for r=0.2, A=3816 and, for r=1, A=7694. This can be expressed as:

$$0.2 \le r \le 1 \text{ and } 3816 \le A \le 7694,$$

and substituting in Equation 1 gives:

$$3816 \le (\lambda_1 - 594 \text{ nm})(\lambda_2 - 425 \text{ nm}) \le 7694$$

Combining all inequalities, the operational range of the first and second wavelength bands may be described as:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}$$

The last two relationships define the wavelength range of the first peak wavelength $\lambda_1$ as a function of the second peak wavelength $\lambda_2$.

Thus, various embodiments disclosed herein may use radiation having parameters including a first peak wavelength in a range from 640 nm to 740 nm, a second peak wavelength in a range from 470 mu to 530 nm, and an intensity ratio of the radiation at the second peak wavelength relative to the radiation at the first peak wavelength in a range from 0.2 to 1. Within these bounds, the first peak wavelength falls within a range given by:

$$\lambda_1 \geq \frac{3816}{\lambda_2 - 425} + 594 \text{ (nm); and}$$

$$\lambda_1 \leq \frac{7694}{\lambda_2 - 425} + 594 \text{ (nm).}$$

The radiation may have a spectral width (e.g. FWHM) in a range from 40 nm to 150 nm. In other embodiments, the radiation may have a spectral width (e.g. FWHM) outside of this range, and may still provide a good contrast between inflamed and uninflamed tissue.

Radiation having the above-identified parameters may be delivered towards skin or tissue of a subject using a tissue illumination system as disclosed herein. Alternatively, white or broadband radiation may be delivered towards the skin or tissue of the subject, and one or more filters may be used to filter the radiation incident on or reflected from the skin or tissue such that the radiation viewed by a viewer has one or more of the above-identified parameters. Examples of various systems that may be used to view tissue of a subject that has been illuminated using radiation having the above-identified parameters are discussed below.

FIG. 7 is a schematic illustration of an example of a tissue illumination system 700, and FIG. 8 is a schematic illustration of a further example of a tissue illumination system 800. The tissue illumination systems 700, 800 comprises at least one radiation source 702 and a radiation delivery unit 704. In the embodiment shown in FIG. 7, the tissue illumination system 700 comprises a single radiation source 702 while, in the embodiment shown in FIG. 8, the tissue illumination system 800 comprises two radiation sources 702*a* and 702*b*. In other examples, more radiation sources may be provided.

In the tissue illumination system 700, the radiation source 702 is configured to generate first radiation in a first wavelength band at a first intensity, the first radiation having a peak wavelength, $\lambda_1$. The peak wavelength of the first radiation is between 640 nm and 740 nm, and the first radiation may have a spectral full-width-at-half-maximum of between 40 nm and 150 nm. The at least one radiation source 702 is also configured to generate second radiation in a second wavelength band at a second intensity, the second radiation having a peak wavelength, $\lambda_2$. The peak wavelength of the second radiation is between 470 nm and 530 nm, and the second radiation may have a spectral full-width-at-half-maximum of between 40 nm and 150 nm. The peak wavelength $\lambda_1$, of the first wavelength band and the peak wavelength $\lambda_2$ of the second wavelength band are selected such that they satisfy the following relationships:

$$\lambda_1 \geq \frac{3816}{\lambda_2 - 425} + 594 \text{ (nm)}$$

-continued $$\lambda_1 \leq \frac{7694}{\lambda_2 - 425} + 594 \text{ (nm).}$$

In some examples, the radiation source 702 may generate multi-band broadband radiation including the first radiation and the second radiation while, in other examples, the radiation source 702 may generate radiation in two distinct wavebands, having the above-mentioned parameters.

In the tissue illumination system 800, the multiple radiation sources 702*a*, 702*b* may each be configured to generate radiation in a different waveband. For example, the radiation source 702*a* may be configured to generate the first radiation in the first wavelength band at the first intensity (e.g. having the corresponding parameters mentioned above) and the radiation source 702*b* may be configured to generate the second radiation in the second wavelength band at the second intensity (e.g. having the corresponding parameters mentioned above).

The radiation delivery unit 704 is configured to deliver the first radiation and the second radiation towards tissue of a subject. The subject may, for example, comprise a person (i.e. a human) who is being examined as part of a medical examination or as part of a personal care or hygiene activity, or who is viewing a representation or a reflection of their own head or body while performing a self-examination for medical reasons or as part of a personal care activity. In other examples, the subject may comprise an animal. As discussed above, when tissue of a subject is viewed under radiation having the above-identified parameters (i.e. under a combination of the first radiation and the second radiation), it is possible to distinguish more clearly between inflamed tissue regions and uninflamed tissue regions.

The radiation delivery unit 704 may be in optical communication with the at least one radiation source 702, such that radiation generated by the radiation source(s) can be delivered towards tissue of the subject. To achieve this, the radiation delivery unit 704 may comprise one or more optical elements.

FIG. 9 is a schematic illustration of an example of the tissue illumination system 700 in use. Radiation (i.e. the first radiation and second radiation) is generated by the at least radiation source 702, and directed via the radiation delivery unit 704 towards tissue 900 of a user. In this example, the tissue 900 includes an uninflamed region 902 and an inflamed region 904. The inflamed region 904 may comprise tissue having a relatively larger amount of blood therein, for example a lip, a bruise or a spot. Radiation may reflect from the tissue 900 towards an eye of a viewer 906. It will be appreciated that the viewer 906 may be the subject whose tissue 900 is being viewed, for example if the viewer is looking at a reflection of their own head or body in a mirror, or looking at a representation of their own head or body in a computing device, such as a tablet computer or smartphone. Alternatively, the viewer 906 may be a person who is not the subject whose tissue 900 is being viewed.

In some embodiments, the first radiation and the second radiation may be generated and/or emitted/delivered towards the tissue of the subject with equal intensities. Thus, the intensity ratio of the second intensity relative to the first intensity may be 1. However, in other embodiments, the second intensity may be less than the first intensity, such that the second radiation is generated, emitted or delivered having intensity is less than that of the first radiation. Thus, the intensity ratio of the first intensity relative to the second intensity may be between 0.2 and 1. In other examples, the intensity ratio of the first intensity relative to the second intensity may be between 0.4 and 0.6. More specifically, particular intensity ratios of 0.2, 0.5 or 1 may be applied in some examples. As will become apparent below, the intensity ratio may be varied based on parameters of ambient light, such as ambient light intensity.

Figure 10:
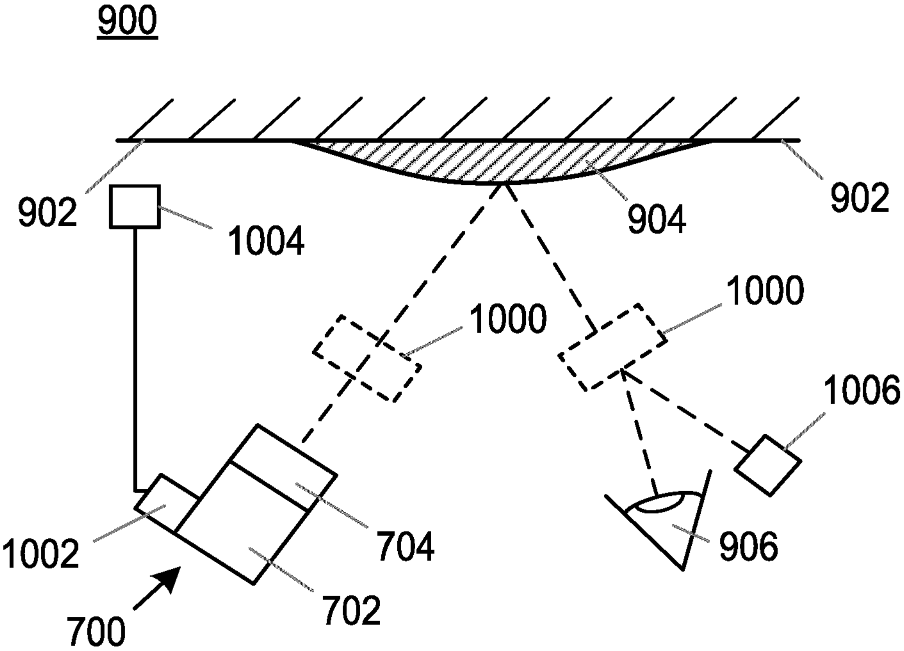
FIG. 10 is a schematic illustration of an example of a tissue illumination system illuminating a region of inflamed tissue.

According to some embodiments, the tissue illumination system 700, 800 may comprise one or more other components, such as optical components, to enhance the contrast between the inflamed and uninflamed tissue regions. For example, the tissue illumination system 700, 800 may comprise a diffuser configured to diffuse radiation (e.g. light) emitted from the radiation source(s) 702. In other examples, the tissue illumination system 700, 800 may comprise one or more polarizers configured to polarize radiation (e.g. light) emitted by the radiation source(s) 702. FIG. 10 is a schematic illustration of an example of the tissue illumination system 700 in use with various optional components. As noted above, the tissue illumination system 700 may, in some embodiments, comprise a polarizer 1000 to linearly polarize the radiation after it is emitted from the at least one radiation source 702 or after the radiation has been reflected from the tissue of the subject thus, the polarizer 1000 may be positioned in one of a number of locations with respect to the radiation source 702 and the viewer 906. As shown in FIG. 10, the polarizer 1000 may be provided a first position such that the radiation emitted by the radiation delivery unit 704 passes through the polarizer before reaching the tissue of the subject, or in a second position such that the radiation passes through the polarizer after reflecting from the tissue of the subject. In some examples, multiple polarizers may be provided (e.g. two polarizers) configured to polarize light in directions orthogonal to one another, in order to reduce specular reflections from the tissue. For example, the tissue illumination system 700, 800 may comprise a first polarizer to linearly polarize the radiation after it is emitted from the at least one radiation source and a second polarizer to linearly polarize, in a direction perpendicular relative to the polarization direction of the first polarizer, radiation reflected from the tissue of the subject. In other words, the first polarizer may linearly polarize the radiation in a first direction after it is emitted from the at least one radiation source and the second polarizer may polarize the radiation in a second direction which is orthogonal to the first direction.

The tissue illumination system 700 may, in some embodiments, further comprise a processor 1002 and/or one or more sensors 1004. The one or more sensors 1004 may be configured to measure a light intensity and/or a color temperature of ambient light at or in the vicinity of the tissue of the subject. The one or more sensors 1004 may, for example, comprise a photometer. The processor 1002 may be operatively coupled to the at least one radiation source 702. The processor 1002 may be configured to adjust, based on an output of the one or more sensors 1004, a parameter of the radiation source or of radiation emitted by the radiation source. For example, the processor 1002 may be configured to adjust, based on an output of the one or more sensors 1004, one or more of an intensity of radiation generated by the at least one radiation source; and an intensity ratio of the first intensity relative to the second intensity. In other embodiments, the processor 1002 may be configured to adjust one or more other parameters in addition to those mentioned above. By adjusting parameters based on measurements recorded using the one or more sensors 1004, it is possible to adjust the radiation delivered towards the tissue of the subject to further enhance the contrast between the inflamed and uninflamed tissue regions, depending on ambient conditions. For example, in bright sunlight, the one or more sensors 1004 may detect that a high ambient brightness and, therefore, the intensity of radiation generated by the radiation source 702, may be increased accordingly. In some examples, one or more sensors may be configured to measure the intensity of radiation in each waveband (e.g. the red and green waveband) separately, and a processor 1002 may be configured to adjust the intensity of radiation generated in one or more of the waveband separately.

The tissue illumination system 700 may, in some embodiments, further comprise an image capture device 1006 configured to receive radiation reflected from the tissue of the subject. The image capture device 1006 may, for example, comprise a charge-coupled device (CCD) or a camera capable of capturing single images or a series of images (e.g. video footage). In this way, an image or images of the tissue of the subject may be recorded and reviewed at a later time. Since the tissue is illuminated using the radiation in two different wavebands, the contrast between any inflamed and uninflamed regions of tissue are distinguishable in the captured image.

The tissue illumination system 700, 800 may comprise a single apparatus or device, with the various components discussed herein forming part of a single integrated unit. In other embodiments, however, the various components may form part of a distributed system, as shown in FIG. 10. One or more of the components of the tissue illumination system 700 discussed herein may form part of a mirror or smart mirror that a user may use to view their face or body. For example, such a mirror may include the radiation source(s) 702, the radiation delivery unit 704, the polarizer 1000, the processor 1002, one or more sensors 1004 and/or the image capture device 1006.

As discussed above, the contrast between inflamed and uninflamed tissue regions may be enhanced by illuminating the tissue with radiation having the particular range of characteristics discussed herein. Specifically, the combination of radiation falling within the red waveband and the green waveband have been found to provide a particularly strong contrast between inflamed and uninflamed tissue regions. As also noted above, the visual contrast may be enhanced by using a filter system to filter broadband radiation (e.g. white light) to significantly filter out any radiation falling outside of the red and green wavebands, or to filter out any radiation that does not have the particular characteristics discussed herein. Thus, in some embodiments, the at least one radiation source comprises a broadband radiation source configured to generate broadband radiation including the first radiation and the second radiation. In other words, the broadband radiation source generates white light which includes the light within the particular wavebands discussed herein. In such embodiments, the radiation delivery unit 704 is configured to deliver the broadband radiation to the tissue of the subject. The tissue illumination system 700 may further comprise at least one filter configured to filter the broadband radiation to filter out radiation having a wavelength falling outside the first wavelength band and radiation having a wavelength falling outside the second wavelength band. Specifically, the at least one filter may be configured to filter the broadband radiation to transmit the first radiation in the first wavelength band at the first intensity, the first radiation having a peak wavelength of between 640 nm and 740 nm, and to transmit the second radiation in the second wavelength band at the second intensity, the second radiation having a peak wavelength of between 470 nm to 530 nm. The first and second radiation may have a spectral full-width-at-half-maximum of between 40 nm and 150 nm.

In some examples, a single filter may be used while, in other examples, two or more filters may be used to provide appropriate filtering of the broadband radiation. Thus, the at least one filter may comprise at least one bandpass filter.

Such an optical filter may, for example, be characterized by its spectral transmission band (i.e. the transmitted wavelength range) and its spectral transmittance (i.e. the amount (e.g. percentage) of radiation transmitted). Therefore, the broadband radiation source may be filtered by an optical filter that is configured to transmit radiation at two spectral bands (e.g. using a dual-band pass filter). Each spectral band may at a different transmittance value, such that the transmitted radiation from the first spectral band of the optical filter at a first optical transmittance is at a first intensity and the transmitted radiation from the second spectral band of the optical filter at a second optical transmittance is at a second intensity.

Figure 11:
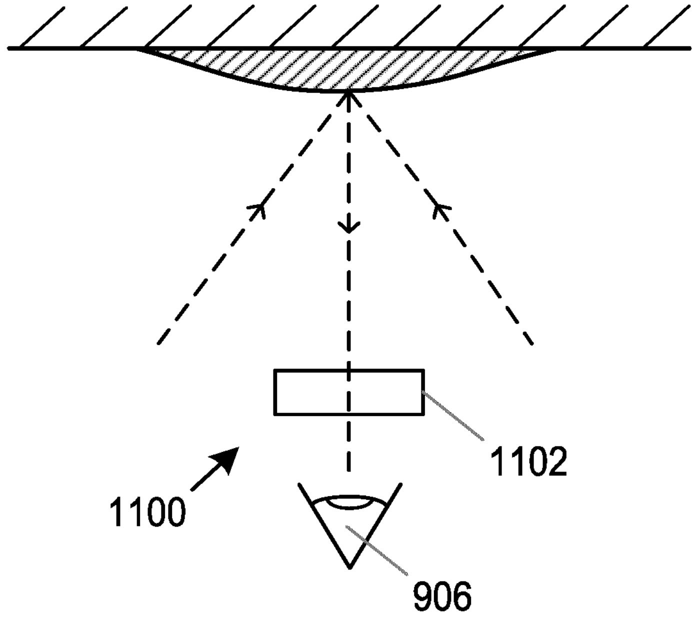
FIG. 11 is a schematic illustration of an example of an optical filter system.

According to a further aspect, the present invention provides an optical filter system. FIG. 11 is a schematic illustration of an example of an optical filter system 1100 that may be used to improve the contrast between uninflamed and inflamed tissue regions of a subject. The optical filter system 1100 comprises at least one bandpass filter 1102. The at least one bandpass filter 1102 is configured to enable transmission of first radiation in a first wavelength band at a first intensity, the first radiation having a peak wavelength, $\lambda_1$, and to enable transmission of second radiation in a second wavelength band at a second intensity, the second radiation having a peak wavelength, $\lambda_2$. The at least one bandpass filter (1102) is configured to enable transmission of the first radiation and the second radiation such that an intensity ratio of the first intensity relative to the second intensity is between 0.2 and 1. The peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

In some examples, the at least one bandpass filter (1102) may be configured to enable transmission of the first radiation and the second radiation such that the first radiation and the second radiation each have a spectral full-width-at-half-maximum of between 40 mu and 150 nm. In some examples, multiple bandpass filters may be provided, for example a first bandpass filter to enable transmission of the first radiation and a second bandpass filter to enable transmission of the second radiation. In use, the tissue of a subject may be illuminated using broadband radiation (e.g. white light) and the optical filter system 1100 may restrict the radiation that it transmits such that a viewer of the tissue, when using the optical filter system, is able to view the inflamed and uninflamed regions of tissue with enhanced contrast.

The optical filter system 1100 may, in some embodiments, comprise a radiation source, such as a broadband radiation source, or a white light source, to direct radiation towards the tissue. Radiation reflected from the tissue may pass through the optical filter system 1100, such that the filtered radiation reaches the viewers eyes. The optical filter system 1100 may be configured and/or positioned to cause spectral filtering of radiation after it is emitted from the radiation source, or to cause spectral filtering of radiation reflected from the tissue of the subject.

In some embodiments, the at least one bandpass filter 1102 is configured to enable transmission of the first radiation and the second radiation such that an intensity ratio of the second intensity relative to the first intensity is between 0.2 and 1.

The optical filter system 1100 may comprise, or form part of, a device or apparatus used by the subject or by a viewer of the subject. Thus, according to a further aspect, the present invention provides a device comprising a tissue illumination system 700, 800 as disclosed herein or an optical filter system 1100 as disclosed herein. The device may, in some embodiments, comprise a medical instrument, a mirror (e.g. a smart mirror), a headset (e.g. smart glasses) or a mask. Such devices may be worn by a viewer of the subject or by the subject itself. In one example, the device may comprise a magnifying device or an optical relay device, incorporated into as a scope for viewing tissue in orifices of the subject, such as the nostril, the mouth or the ear canal. Such a device may incorporate a tissue illumination system 700, 800 or an optical filter system 1100 as disclosed herein, to enable a user of the device to identify inflamed tissue.

Figure 12:
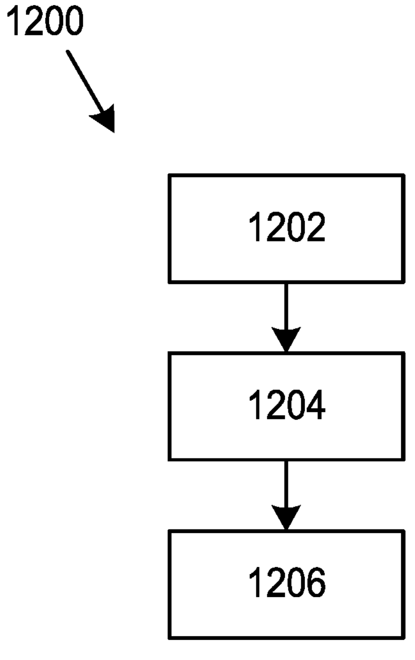
FIG. 12 is a flowchart of an example of a tissue illumination method.

According to a further aspect, the present invention provides a tissue illumination method. FIG. 12 is a flowchart of an example of a method 1200, such as a tissue illumination method. The method 1200 may, for example, be performed using the tissue illumination system 700, 800 disclosed herein. The method 1200 comprises, at step 1202, generating first radiation in a first wavelength band at a first intensity, the first radiation having a peak wavelength, $\lambda_1$. At step 1204, the method 1200 comprises generating second radiation in a second wavelength band at a second intensity, the second radiation having a peak wavelength, $\lambda_2$. An intensity ratio of the first intensity relative to the second intensity is between 0.2 and 1, and the peak wavelength $\lambda_1$, of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

The method 1200 comprises, at step 1206, delivering the radiation in the first radiation and the second radiation towards tissue of a subject. The delivered radiation may then be viewed by a viewer, and the combination of the first and second radiation may enhance the contrast between any inflamed and uninflamed regions of tissue, enabling the viewer to better distinguish between such regions.

The method 1200 may, in some embodiments, further comprise measuring one or more of a light intensity and a color temperature of ambient light at or in the vicinity of the tissue of the subject. The method 1200 may further comprise adjusting, based on the measured light intensity and/or on the measured color temperature, one or more of an intensity of the first radiation and/or the second radiation, and an intensity ratio of the first intensity relative to the second intensity. In this way, the regions of tissue of the subject and, in particular, the contrast between such regions, maybe even more clearly distinguishable to a viewer.

In some embodiments, the method 1200 may further comprise capturing an image of the tissue of the subject after the radiation has been reflected from the tissue. In this way, the image of the tissue of the user may be viewed later time by a viewer, and the improved contrast between the inflamed and uninflamed regions of tissue may be captured.

The at least one radiation source may, in some embodiments, comprise a broadband radiation source configured to generate broadband radiation including radiation in the first wavelength band and radiation in the second wavelength band. In such embodiments, delivering the radiation may comprise delivering the broadband radiation towards tissue of a subject. The method may further comprise filtering the broadband radiation to filter out radiation having a wavelength falling outside the first wavelength band and radiation having a wavelength falling outside the second wavelength band.

More specifically, the method may further comprise filtering the broadband radiation to allow transmission of first radiation in a first wavelength band at a first intensity, the first radiation having a peak wavelength of between 640 nm and 740 nm, and second radiation in a second wavelength band at a second intensity, the second radiation having a peak wavelength of between 470 nm to 530 nm. The method may, in some embodiments, comprise filtering the broadband radiation to allow transmission of first radiation and second radiation having a spectral full-width-at-half-maximum of between 40 nm and 150 nm.

Figure 13:
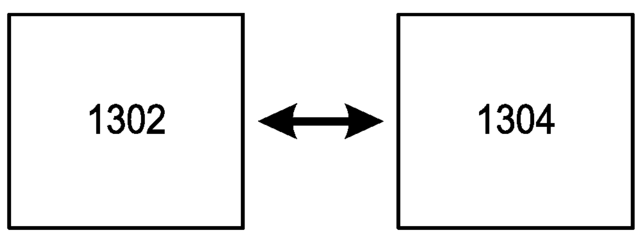
FIG. 13 is a schematic illustration of a processor in communication with a computer-readable medium.

According to a further aspect, the present invention provides a computer program product. FIG. 13 is a schematic illustration of an example of a processor 1302 communication with a computer-readable medium 1304. In various embodiments, a computer program product comprises a non-transitory computer-readable medium 1304, the computer-readable medium having computer-readable code embodied therein, the computer-readable code being configured such that, on execution by a suitable computer or processor 1302, the computer or processor is caused to operate at least one light source to generate first radiation in a first wavelength band at a first intensity to be delivered to tissue of a subject, the first radiation having a peak wavelength, $\lambda_1$; and operate the at least one light source to generate second radiation in a second wavelength band at a second intensity to be delivered to the tissue of a subject, the second radiation having a peak wavelength, $\lambda_2$. An intensity ratio of the first intensity relative to the second intensity is between 0.2 and 1. The peak wavelength $\lambda_1$, of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

The first radiation and the second radiation may each have a spectral full-width-at-half-maximum of between 40 nm and 150 nm. More generally, the computer-readable code may be configured such that, on execution by the processor 1302, the processor is configured to perform one or more steps of the method 1200 disclosed herein. The processor 1302 may comprise the processor 1002 discussed above.

In some embodiments, the computer-readable code may be further configured such that, on execution by a suitable computer or processor 1302, the computer or processor is caused to receive sensor data indicative of a light intensity and/or a color temperature of ambient light at or in the vicinity of the tissue of the subject; and adjust, based on the received sensor data, one or more of: an intensity of radiation generated by the at least one radiation source; and an intensity ratio of the second intensity relative to the first intensity. The sensor data may, for example, comprise data acquired and/or received from the one or more sensors 1004 discussed above.

The processor 1002, 1302 can comprise one or more processors, processing units, multi-core processors or modules that are configured or programmed to control components of the systems 700, 800, 800 in the manner described herein. In particular implementations, the processor 1002, 1302 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk.

Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

The present invention can also be described as worded in the following clauses:

Clause 1. A tissue illumination system (700, 800) comprising:

at least one radiation source (702) configured to generate:

first radiation in a first wavelength band at a first intensity, the first radiation having a peak wavelength, $\lambda_1$; and second radiation in a second wavelength band at a second intensity, the second radiation having a peak wavelength, $\lambda_2$; and a radiation delivery unit (404) configured to deliver the first radiation and the second radiation towards tissue of a subject;

wherein an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

Clause 2. A tissue illumination system (700, 800) according to clause 1, wherein the first radiation and the second radiation each has a spectral full-width-at-half-maximum of between 40 nm and 150 nm.

Clause 3. A tissue illumination system (700, 800) according to clause 1 or clause 2, wherein the at least one radiation source comprises a broadband radiation source configured to generate broadband radiation including the first radiation and the second radiation;

wherein the radiation delivery unit is configured to deliver the broadband radiation to the tissue of the subject; and wherein the tissue illumination system further comprises:

at least one filter configured to filter the broadband radiation to filter out radiation having a wavelength falling outside the first wavelength band and radiation having a wavelength falling outside the second wavelength band.

Clause 4. A tissue illumination system (700, 800) according to clause 3, wherein the at least one filter comprises at least one bandpass filter.

Clause 5. A tissue illumination system (700, 800) according to any of the preceding clauses, further comprising:

a polarizer to linearly polarize the radiation after it is emitted from the at least one radiation source or after the radiation has been reflected from the tissue of the subject.

Clause 6. A tissue illumination system (700, 800) according to any of the preceding clauses, further comprising:

one or more sensors configured to measure a light intensity and/or a color temperature of ambient light at or in the vicinity of the tissue of the subject; and a processor operatively coupled to the at least one radiation source, the processor configured to adjust, based on an output of the one or more sensors, one or more of:

an intensity of radiation generated by the at least one radiation source; and an intensity ratio of the first intensity relative to the second intensity.

Clause 7. A tissue illumination system according to any of the preceding clauses, further comprising:

an image capture device configured to receive radiation reflected from the tissue of the subject.

Clause 8. An optical filter system (1100) comprising:

at least one bandpass filter (1102) configured to enable transmission of:

first radiation in a first wavelength band at a first intensity, the first radiation having a peak wavelength, $\lambda_1$; and second radiation in a second wavelength band at a second intensity, the second radiation having a peak wavelength, $\lambda_2$;

wherein the at least one bandpass filter (1102) is configured to enable transmission of the first radiation and the second radiation such that an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

Clause 9. An optical filter system (800) according to clause 8, wherein the at least one bandpass filter (802) is configured to enable transmission of the first radiation and the second radiation such that the first radiation and the second radiation each have a spectral full-width-at-half-maximum of between 40 nm and 150 nm.

Clause 10. A device comprising a tissue illumination system (700, 800) or an optical filter system (1100) according to any of the preceding clauses, wherein the device comprises a medical instrument, a mirror, a headset or a mask.

Clause 11. A tissue illumination method (1200) comprising:

generating (1202) first radiation in a first wavelength band at a first intensity, the first radiation having a peak wavelength, $\lambda_1$;

generating (1204) second radiation in a second wavelength band at a second intensity, the second radiation having a peak wavelength, $\lambda_2$; and delivering (1206) the radiation in the first radiation and the second radiation towards tissue of a subject;

wherein an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

Clause 12. A tissue illumination method (1200) according to clause 11, further comprising:

measuring one or more of a light intensity and a color temperature of ambient light at or in the vicinity of the tissue of the subject; and adjusting, based on the measured light intensity and/or on the measured color temperature, one or more of an intensity of the first radiation and/or the second radiation, and an intensity ratio of the first intensity relative to the second intensity.

Clause 13. A computer program product comprising a non-transitory computer-readable medium (1304), the computer-readable medium having computer-readable code embodied therein, the computer-readable code being configured such that, on execution by a suitable computer or processor (1302), the computer or processor is caused to:

operate at least one light source to generate first radiation in a first wavelength band at a first intensity to be delivered to tissue of a subject, the first radiation having a peak wavelength, $\lambda_1$; and operate the at least one light source to generate second radiation in a second wavelength band at a second intensity to be delivered to the tissue of a subject, the second radiation having a peak wavelength, $\lambda_2$;

wherein an intensity ratio of the first intensity relative to the second intensity is between 0.2 and 1; and wherein the peak wavelength $\lambda_1$, of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

Clause 14. A computer program product according to clause 13, wherein the first radiation and the second radiation each has a spectral full-width-at-half-maximum of between 40 nm and 150 nm.

Clause 15. A computer program product according to clause 13 or clause 14, wherein the computer-readable code is further configured such that, on execution by a suitable computer or processor (1302), the computer or processor is caused to:

receive sensor data indicative of a light intensity and/or a color temperature of ambient light at or in the vicinity of the tissue of the subject; and adjust, based on the received sensor data, one or more of:

an intensity of radiation generated by the at least one radiation source; and an intensity ratio of the first intensity relative to the second intensity.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A tissue illumination system comprising:

at least one radiation source configured to generate dual-colored radiation with:

first radiation in a first wavelength band at a first intensity, the first radiation having a peak wavelength, $\lambda_1$; and second radiation in a second wavelength band at a second intensity, the second radiation having a peak wavelength, $\lambda_2$; and a radiation delivery unit configured to deliver the first radiation and the second radiation towards tissue of a subject;

wherein an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

2. A tissue illumination system according to claim 1, wherein the first radiation and the second radiation each has a spectral full-width-at-half-maximum of between 40 nm and 150 nm.

3. A tissue illumination system according to claim 1, further comprising:

a polarizer to linearly polarize the radiation after it is emitted from the at least one radiation source or after the radiation has been reflected from the tissue of the subject.

4. A tissue illumination system according to claim 1, further comprising:

one or more sensors configured to measure a light intensity and/or a color temperature of ambient light at or in the vicinity of the tissue of the subject; and a processor operatively coupled to the at least one radiation source, the processor configured to adjust, based on an output of the one or more sensors, one or more of:

an intensity of radiation generated by the at least one radiation source; and an intensity ratio of the first intensity relative to the second intensity.

5. A tissue illumination system according to claim 1, further comprising:

an image capture device configured to receive radiation reflected from the tissue of the subject.

6. The device comprising a tissue illumination system according to claim 1 or an optical filter system, wherein the device comprises a medical instrument, a mirror, a headset or a mask.

7. An optical filter system comprising:

at least one bandpass filter configured to enable transmission of:

first radiation in a first wavelength band at a first intensity, the first radiation having a peak wavelength, $\lambda_1$; and second radiation in a second wavelength band at a second intensity, the second radiation having a peak wavelength, $\lambda_2$;

wherein the at least one bandpass filter is configured to enable transmission of the first radiation and the second radiation such that an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

8. An optical filter system according to claim 7, wherein the at least one bandpass filter is configured to enable transmission of the first radiation and the second radiation such that the first radiation and the second radiation each have a spectral full-width-at-half-maximum of between 40 nm and 150 nm.

9. A device comprising:

a tissue illumination system comprising:

at least one radiation source wherein the at least one radiation source comprises a broadband radiation source configured to generate broadband radiation including:

first radiation having a wavelength, $\lambda_1$; and second radiation having a peak wavelength, $\lambda_2$; and a radiation delivery unit configured to deliver the broadband radiation to the tissue of the subject; and the optical filter system according to claim 7 wherein the optical filter system is positioned to filter the broadband radiation after the broadband radiation is emitted from the at least one radiation source and before it is reflected from the tissue of the subject.

10. A device comprising:

a tissue illumination system comprising:

at least one radiation source wherein the at least one radiation source comprises a broadband radiation source configured to generate broadband radiation including:

first radiation having a wavelength, $\lambda_1$; and second radiation having a peak wavelength, $\lambda_2$; and a radiation delivery unit configured to deliver the broadband radiation to the tissue of the subject; and the optical filter system according to claim 7 wherein the optical filter system is positioned to filter the broadband radiation after the radiation has been reflected from the tissue of the subject.

11. A tissue illumination method comprising:

generating first radiation in a first wavelength band at a first intensity, the first radiation having a peak wavelength, $\lambda_1$;

generating second radiation in a second wavelength band at a second intensity, the second radiation having a peak wavelength, $\lambda_2$; and delivering the dual-colored radiation in the first radiation and the second radiation towards tissue of a subject;

wherein an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

12. A tissue illumination method according to claim 11, further comprising:

measuring one or more of a light intensity and a color temperature of ambient light at or in the vicinity of the tissue of the subject; and adjusting, based on the measured light intensity and/or on the measured color temperature, one or more of an intensity of the first radiation and/or the second radiation, and an intensity ratio of the first intensity relative to the second intensity.

13. A computer program product comprising a non-transitory computer-readable medium, the computer-readable medium having computer-readable code embodied therein, the computer-readable code being configured such that, on execution by a suitable computer or processor, the computer or processor is caused to:

operate at least one light source to generate dual-colored radiation with first radiation in a first wavelength band at a first intensity to be delivered to tissue of a subject, the first radiation having a peak wavelength, $\lambda_1$; and second radiation in a second wavelength band at a second intensity to be delivered to the tissue of a subject, the second radiation having a peak wavelength, $\lambda_2$;

wherein an intensity ratio of the first intensity relative to the second intensity is between 0.2 and 1; and wherein the peak wavelength $\lambda_1$ of the first wavelength band and the peak wavelength $\lambda_2$ of the second wavelength band are selected such that they satisfy the following relationships:

$$\begin{cases} 640 \le \lambda_1 \le 740 \text{ (nm)} \\ 470 \le \lambda_2 \le 530 \text{ (nm)} \\ \lambda_1 \ge \dfrac{3816}{\lambda_2 - 425} + 594 \text{ (nm)} \\ \lambda_1 \le \dfrac{7694}{\lambda_2 - 425} + 594 \text{ (nm)} \end{cases}.$$

14. A computer program product according to claim 13, wherein the first radiation and the second radiation each has a spectral full-width-at-half-maximum of between 40 nm and 150 nm.

15. A computer program product according to claim 13, wherein the computer-readable code is further configured such that, on execution by a suitable computer or processor, the computer or processor is caused to:

receive sensor data indicative of a light intensity and/or a color temperature of ambient light at or in the vicinity of the tissue of the subject; and adjust, based on the received sensor data, one or more of:

an intensity of radiation generated by the at least one radiation source; and an intensity ratio of the first intensity relative to the second intensity.

* * * * *